United States Patent [19]
Vrabel

[11] Patent Number: 5,009,225
[45] Date of Patent: Apr. 23, 1991

[54] PERSONAL VENTILATING SYSTEM
[75] Inventor: William S. Vrabel, Warsaw, Ind.
[73] Assignee: Boehringer Mannheim Corporation, Indianapolis, Ind.
[21] Appl. No.: 443,916
[22] Filed: Nov. 30, 1989
[51] Int. Cl.$^5$ .............................................. A62B 7/00
[52] U.S. Cl. .......................... 128/201.24; 128/201.23; 128/200.24; 128/202.19
[58] Field of Search ...................... 128/200.24, 201.24, 128/201.25, 201.15, 202.19, 204.23, 204.15, 201.23

[56] References Cited
U.S. PATENT DOCUMENTS

| | | |
|---|---|---|
| 2,332,662 | 10/1943 | Nathanson . |
| 3,955,570 | 5/1976 | Hutter, III .................... 128/201.23 |
| 4,019,508 | 4/1977 | Der Estephanian et al. ... 128/202.19 |
| 4,055,173 | 10/1977 | Kuab .................... 128/847 |
| 4,239,039 | 12/1980 | Thompson . |
| 4,296,746 | 10/1981 | Mason, Jr. et al. .................... 55/162 |
| 4,331,141 | 5/1987 | Pokhis .................... 128/204.28 |
| 4,534,344 | 8/1985 | Constance-Hughes ........ 128/201.15 |
| 4,590,591 | 5/1986 | O'Connor .................... 128/204.23 |
| 4,627,860 | 12/1986 | Rowland .................... 128/205.24 |
| 4,730,612 | 3/1988 | Dampney .................... 128/201.24 |
| 4,901,716 | 2/1990 | Stackhouse et al. ............ 128/201.25 |
| 4,903,694 | 2/1990 | Hager .................... 128/204.15 |

OTHER PUBLICATIONS

Brochure entitled "Sterile View TM Surgical Exhaust System", 4 pages, DePuy.
Brochure entitled "Critical Protection for Surgical Environments Infection Control Systems", 6 pages De-Puy.
"Sterile-View TM Surgical Helmet (5411-00) Adjustment Instructions", 1 sheet, revised 10-82, DePuy.
"Sterile View TM Back Pack System Operations Manual-Direction's for Use", 2 sheets (4 pages), De-Puy.

Primary Examiner—Edgar S. Burr
Assistant Examiner—Eric P. Raciti
Attorney, Agent, or Firm—Perman & Green

[57] ABSTRACT

A personal exhaust system for individual use by the members of a surgical team in an operating room. It may be employed in conjunction with a disposable hood or combination hood and gown worn by each such person. Each system includes a d.c. powdered motor and blower unit adapted to be connected, via a light weight power cord to an a.c.-to-d.c. converter and transformer, or switching mode power supply. A filter is utilized to remove contaminants from the air before it exhausts to the atmosphere. Each unit is provided with its own on-off switch and the flow of air for each unit is individually controlled. A battery back-up allows for short excursions away from the power supply. In another embodiment, fresh filtered air may be directed into the hood simultaneously with removal of stale air from the hood and its subsequent filtered exhaustion to the atmosphere.

4 Claims, 3 Drawing Sheets

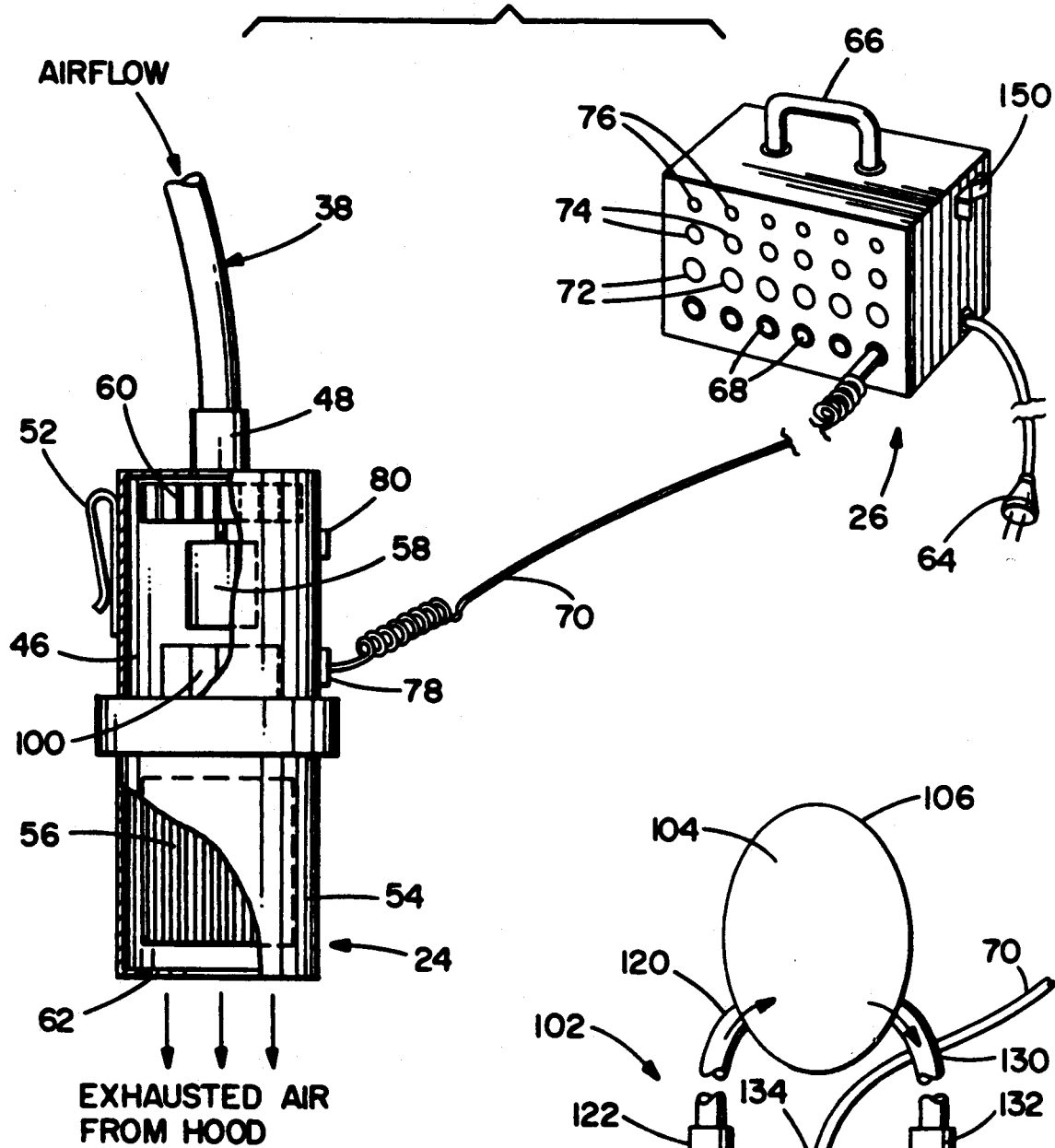

PERSONAL VENTILATING SYSTEM

BACKGROUND OF THE INVENTION

I. Field of the Invention

The present invention relates to surgical ventilating systems for drawing stale air away from members of the surgical team while protecting a patient from contamination. The invention also relates to ventilating systems which simultaneously protect members of the surgical team from contamination.

II. Discussion of the Prior Art

This invention generally lies in the field of masking systems to prevent contamination of the air in any location where it is desired to maintain "clean air" conditions to avoid corrosion or deposit of dust or moisture or other contaminants. It is more particularly directed to a masking system for use in the performance of surgical operations.

One of the problems which has plagued the medical profession for many years is post-operative infection resulting from contamination of open wounds during surgery. There are many possible causes of such contamination, such as contaminated instruments and hands, perspiration and respiratory droplets and shedding of hair and skin of the surgeon or other operating team member, and the bacteria on the skin of the patient. Most of these problems have been greatly reduced by presently used techniques, including preoperative skin cleaning, the surgical scrub, rubber gloves, masks, sterile drapes, clothing, and instruments, and thorough filtration of the air in the operating theater. However, some contamination and infection still exists, and efforts are continually being made to improve the situation.

One of the sources of contamination which is very difficult to control is the surgeon himself and his operating team. Of necessity, he and they must be immediately adjacent the patient and in fact, leaning directly over the locus of the surgery. His gown and hood are not totally impervious to passage of perspiration moisture and epithelial scales and bacteria from the body. The conventional surgical mask is merely a coarse filter which removes bacteria laden droplets of moisture from the exhaled breath. This mask soon becomes saturated with water preventing easy passage of air through the material. The exhaled air is thus directed out around the edges of the mask. This re-direction of moist air upward around the nose and cheeks causes fogging of spectacles and general discomfort to the surgeon.

Considerable improvement has resulted from equipping operating rooms with means for producing a continuous laminar flow of sterile air through the room from one side wall to the opposite wall or from ceiling to floor. The flow carries the majority of contaminants out of the room before they can come into contact with the patient, but every movement of any member of the operating team disturbs the laminar flow and reduces its effectiveness. In addition, the surgical team working in close proximity to the surgical site provides a concentrated source of bacteria which can be carried by the flowing air into the wound.

An answer to this problem has been the provision of exhaust type masking systems in which each member of the operative team is substantially completely covered with a hood and gown of practically impermeable material and closed transparent mask located in an opening in the front of the hood. A conduit system is connected to a suction manifold and has a suction opening adjacent the face of the wearer to carry away exhalations, perspiration, and the like. There is negative pressure throughout the interior of the gown so that any leakage is inward. Such a system is disclosed in U.S. Pat. No. 3,955,570.

In such systems, in order to effectively draw off the emanated contaminants through a suction hose connected to the gown or hood, a relatively large vacuum blower has been required which creates excessive and annoying noise and impairs communication among members of the operating team. These latter systems often times use multiple outlets on a distribution manifold for the attachment of a plurality of hoses, then vent the exhaust air outside of the operating room. In other instances, as disclosed in U.S. Pat. No. 4,055,173, the exhaust air is vented, via the hoses, through a filtering unit physically located within the operating room.

Also known are gowns and masks into which are incorporated battery powered motor/blower assemblies worn by each individual, thereby eliminating the need for the cumbersome hoses. However, even in these instances, there are drawbacks which include the limited useful life for, and the substantial weight of, the batteries. During a lengthy surgical procedure, the batteries can lose much or all of their power, and their substantial weight can tire the members of the surgical team after a time.

Although in the past, the emphasis has been placed on protecting the patient from contamination, more recently, primarily because of the substantial concerns raised by the AIDS virus, there has been more and more emphasis on protecting the surgical team in the operating room from contamination as well as the patient.

It was with knowledge of the prior art, its limitations, and concerns with existing equipment that the present invention was conceived and has now been reduced to practice.

SUMMARY OF THE INVENTION

The present invention relates to a personal exhaust system for individual use by the members of a surgical team in an operating room. It may be employed in conjunction with a disposable hood or combination hood and gown worn by each such person. Each system includes a d.c. powered motor and blower unit adapted to be connected, via a light weight power cord, to an a.c.-to-d.c. converter and transformer, or switching mode power supply. Each unit is provided with its own on-off switch and the flow of air for each unit is individually controlled. A battery back-up allows for short excursions away from the power supply. A filter is utilized to remove contamination from the air before it exhausts to the atmosphere. In another embodiment, fresh filtered air may be diverted into the hood simultaneously with removal of stale air from the hood and its subsequent filtered exhaustion to the atmosphere.

Accordingly, it is an object of the present invention to provide a surgical masking and ventilating system that is adapted to more efficiently and effectively remove contaminants emitted from members of the operating team. A related object is to simultaneously protect members of the operating team from contaminants present in the operation room.

Another object is to provide a masking and ventilating system as characterized above which operates quietly so as not to interfere with communications among the surgical team.

A further object is to provide a surgical masking and ventilating system as characterized above which may be conveniently used by members of the operating team without substantially restricting their movement or vision.

Still another object is to provide such a masking and ventilating system that is selectively adjustable to permit desired amount of ventilation and cooling for comfort of the user.

Other features and benefits of the invention can be enumerated as follows. By using a d.c. electrical power supply, the invention overcomes the lack of lightweight battery power and the need to replace batteries for continuous long term operation. Also, the electrical power supply provides continuous energy to generate sufficient air movement for comfort of the wearer. Variable speed control provides for adjustment by each wearer to assure his or her own comfort level. At the same time, built-in batteries provide a level of airflow sufficient to provide adequate air flow during necessary short term movement away from the electrical power supply. Cumbersome exhaust hoses of the prior art are replaced by lightweight, coiled electrical cords allowing greater freedom of movement. Each user of the inventive system wears an individual light weight unit with an attached filter as compared to the portable units with heavy long term battery packs which are presently being used. The electrical power supply is also adequate to operate other accessories commonly associated with surgical hoods and gowns such as a helmet mounted light or an individual wireless communication device.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate different embodiments of the invention, and, together with the description, serve to explain the principles of the invention in general terms. Like numerals refer to like parts throughout the disclosure.

BRIEF DESCRIPTION OF THE DRAWINGS

FIG. 2 is a diagrammatic view, partially perspective and illustrating, in greater detail, certain of the components illustrated in FIG. 1; and FIG. 3 is a diagrammatic view of another embodiment of the invention.

DETAILED DESCRIPTION OF THE INVENTION

Figure 1:
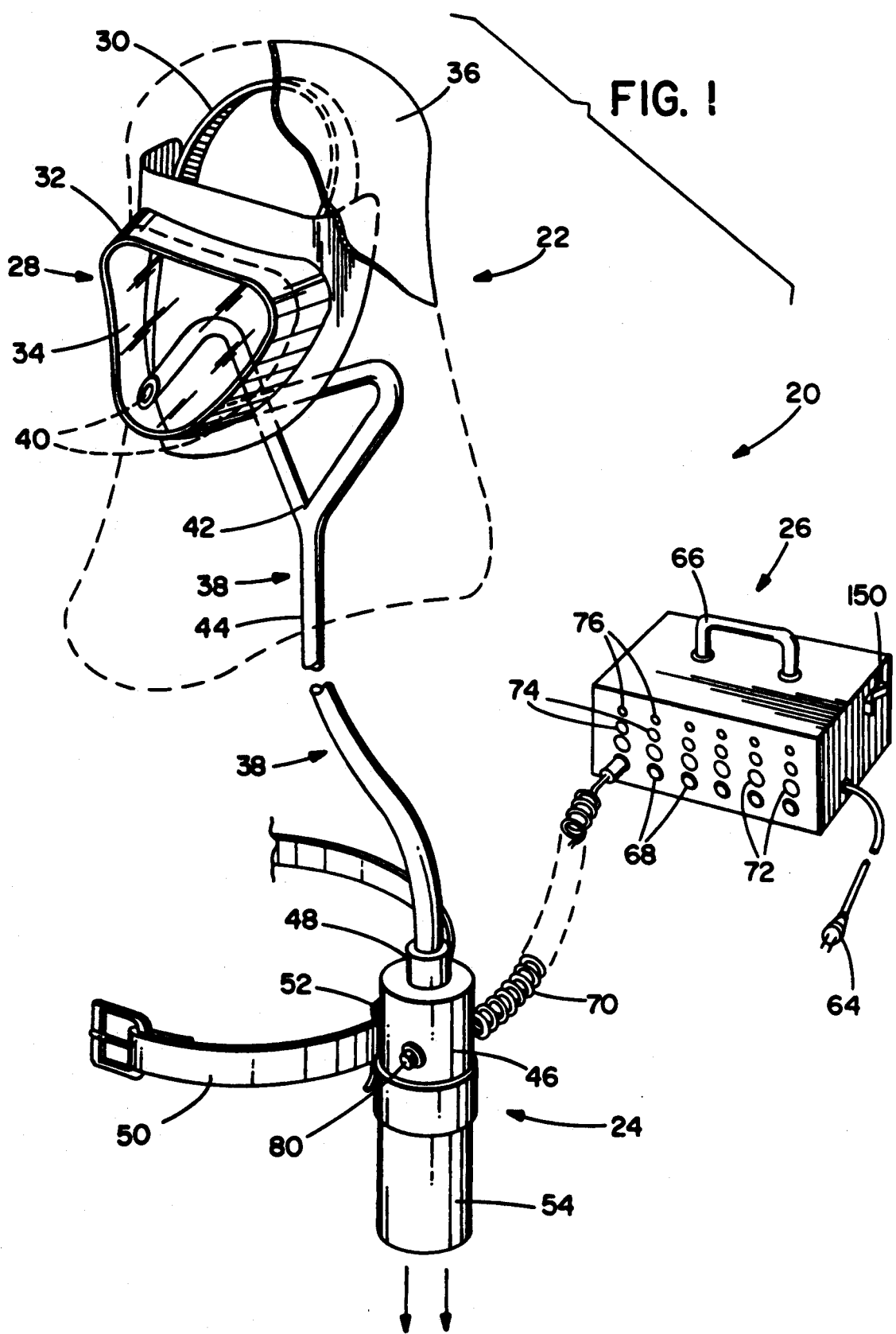
FIG. 1 is a perspective view illustrating the components of the personal ventilating system of the invention.

Turn now to the drawings and, initially, to FIG. 1 which illustrates one embodiment of the invention. In this embodiment, a personal ventilating system 20 includes a surgical hood 22, an adjustable flow inducing mechanism 24, and a suitable power source 26.

The hood 22 may be of the type disclosed in U.S. Pat. No. 3,955,570, the disclosure of which is incorporated herein in its entirety by reference. The surgical hood 22 is seen to include a support member 28 which is sized and shaped to fit on the head of the wearer who, presumably, would be a member of the surgical team. The support member 28 includes at least one head band 30 which is adapted to generally envelope the head. Although not illustrated, the head band 30 may be adjustable to fit a variety of sizes of heads. The support member 28 also includes a substantially rigid frame 32 to which is suitably mounted a transparent face plate 34. The face plate 34, which may be of glass, plastic, or other suitable transparent material, is preferably spherically shaped to provide the wearer with optimum visibility. To this end, the face plate 34 is substantially coextensive with the face of the wearer.

The surgical hood 22 also includes a hood garment 36 composed of flexible sheet material, preferably of a suitable paper or non-woven fabric. The hood garment 36 is suitably attached to the support member 28 and is provided with an opening which is sized and shaped to enable the frame 32 to protrude while assuring a substantially sealing fit with the frame. In an alternate construction, the hood and face plate may be integral. The garment 36 is draped over the shoulders of the wearer and may be as long as desired, even extending down to the footwear of the surgical team member. It may even be used in combination with surgical pants made of a similar material.

A suction ventilation conduit 38 is associated with the support member 28 and may be made partly of rigid material and partly of flexible material, as desired, to assure comfort for the wearer as well as operability of the system. As illustrated in FIG. 1, the conduit 38 includes a pair of spaced apart inlet members 40 which are supportively fastened to the frame 32, then extend rearwardly and downwardly away from the face plate 34 until they are joined at a Y-location 42 to a single length 44 of the conduit.

With continued reference to FIG. 1, the adjustable flow inducing mechanism 24 is seen to include an outer casing 46. A distant end of the conduit 38 is sealingly attached to a projecting port member 48 integral with the outer casing. The outer casing 46 can be removably attached to a belt 50 of the wearer by means of a belt clip 52. A filter housing 54 may be removably joined to the outer casing 46 by means of screw threads (not shown) or some other suitable attachment device. A filter housing 54 serves to retain in position an HEPA (high efficiency particulate air) filter. In a typical system, the filter 56 may be of a construction to provide a 99.97% efficiency in removing particles down to 0.3 micron size.

A d.c. motor 58 is mounted within the outer casing 46 and is operably connected to a suitable fan 60 for drawing air through the ventilation conduit 38 from the space enclosed by the face plate 34 and causing it to exhaust through an outlet 62 at an extremity of the filter housing 54 after flowing through the filter 56. In an alternate construction, the outlet from the filter may be located around its periphery, even for its entire length.

The power source 26 includes an a.c.-to-d.c. converter and transformer, which, alternatively, may be referred to as a d.c. switching mode power supply. In any event, the power source 26 would customarily be energized via a plug 64 insertable into a normal electrical mains outlet. The power source 26 is provided with a handle 66 to enable it to be easily carried from place to place. One example of a power supply which would be suitable for purposes of the invention is Model No. RAX12-25K sold by KEPKO Inc. of Flushing, N.Y.

As illustrated in FIG. 2, the power source 26 has provision for powering the flow inducing mechanisms 24 for six different surgical team members. For each team member, the power source 26 includes a receptacle 68 for reception of a suitable connector at one end of a light weight coiled power cord 70, a variable speed control knob 72, an on/off switch 74, and a power usage lamp 76 for indicating whether the switch 74 is turned "on" or "off". An alternative construction may provide a non-coiled power cord with an associated take-up mechanism to minimize the amount of excess cord. A connector at an opposite end of the power cord 70 is similarly releasably connected to a suitable receptacle 78 on the outer casing 46 so as to electrically connect the motor 58 to the power source 26. Thus, when the cord 70 electrically joins the power source 26 to the motor 58, it is effective to energize the motor and thereby cause flow of air from the space behind the face plate 34 to the surrounding atmosphere beyond the outlet 62 of the filter housing 54. An on/off switch 80 is also provided at the outer casing 46 to enable the wearer to conveniently turn on or turn off the motor 58 when distant from the power source 26. Each of the control knobs 72 serves to control the flow rate of the air being drawn from the space enclosed by the transparent face plate 34 and exhausted through the outlet 62. Specifically, the speed control 72 serves to adjust the voltage being directed to the motor 58 and, therefore, its speed. Thus, each member of the surgical team can adjust the flow rate to accommodate his or her own personal preference.

The coiled power cord 70 is of a length adequate to enable the wearer of the mechanism 24 to move freely around the operating room. However, provision is made to enable the wearer to leave the proximity of the power source 26 for a short period of time, for example, for up to a 20 to 30 minute time period without removing the surgical hood 22. Specifically, a back-up battery 100 is provided within the outer casing 46 capable of electrical connection to the motor 58 upon removal of the power cord 70 from the receptacle 78. The battery 100 may be, for example, a rechargeable sealed nickel cadmium alkaline cell which is considerably smaller and lighter than the sealed lead acid rechargeable batteries which have commonly been used with known portable ventilating systems. This is for the reason that the battery 100 is not intended for long term service but only for temporary use when the mechanism 24 is not to be connected to the power source 26.

Another embodiment of the invention is illustrated in FIG. 3 which depicts a dual protection adjustable flow inducing mechanism 102. While efforts to protect a patient in the operating room against contamination during a surgical procedure have long been emphasized, it is only relatively recently that any substantial emphasis has been placed on protection of the members of the surgical team. A particularly strong influence in this regard has been the rapid spread of the AIDS virus. The mechanism 102 has been devised to provide a system which is protective of both the patient and the surgical team. In this embodiment, a surgical hood diagrammatically represented at 104 is provided which may be substantially similar to the hood 22. However, in this instance, a suitable seal is schematically represented at 106 as a construction in which the space enclosed by the face plate is suitably isolated from the atmosphere. In this instance, the hood garment of the surgical hood 104 may be composed of a material which is impermeable to the surrounding atmosphere such that the only air received therein is that which is permitted in by reason of the mechanism 102. To this end, an outer casing 108 encloses a pair of flow subsystems, 110 and 112. The first flow subsystem serves to deliver filtered air from the atmosphere to the surgical hood 104. A second flow subsystem 112 serves to exhaust filtered air to the atmosphere from the surgical hood 104.

Each flow subsystem 110, 112 is generally of the construction of the previously described flow inducing mechanism 24. The flow subsystem 110 includes a fan 114 driven by a d.c. motor 116. An HEPA filter 118, similar to filter 56, is also provided in the manner of the mechanism 24. Additionally, a pressurized ventilation conduit 120 is sealingly connected via a projecting port member 122 to the outer casing 108 and serves to introduce air from the surrounding atmosphere into the surgical hood 104, particularly in the region of the face plate 34. In a similar manner, the flow subsystem 112 includes a fan 124, a d.c. motor 126 for driving the fan, and an HEPA filer 128. Also, a suction ventilation conduit 130 is sealingly connected to the casing 108 via a projecting port member 132 and serves to draw air from the surgical hood 104 and particularly from the region behind the face plate. The power cord 70 is selectively connected to a receptacle 134 on the outer casing 108 to provide d.c. power to the motors 116, 126 as desired. However, as in the instance of the mechanism 24, when the wearer of the mechanism 102 chooses to leave the vicinity of the power source 26, the cord 70 can be withdrawn from the fitting 134 and a backup battery 136 is then operable to simultaneously energize the motors 116, 126. For convenience, in the alternative, it might be desirable to provide a quick disconnect connector on the cord at the approximate bottom of the wearer's pant leg. This would avoid the necessity of reaching under the garment 36 for this purpose which may prove difficult under certain circumstances. Again, in the manner of the mechanism 24, the mechanism 102 includes an on/off switch 138 enabling the wearer to turn the mechanism 102 on or off without having to travel to a remote location.

As the mechanism 102 is operated, air from the surrounding atmosphere is drawn in through a suitable inlet duct 140 at flow subsystem 110. The air passes through the filter 118 where it is cleansed of impurities, then passes through conduit 120 into the surgical hood 104. Simultaneously, stale air is drawn from the surgical hood through the conduit 130, through the filter 128 and out through a suitable exhaust duct 142. In this manner, the air being breathed by the wearer of the mechanism 102 is purified and, simultaneously, air being exhausted into the surrounding atmosphere which is the air being breathed by a patient undergoing surgery, is similarly purified.

As in the instance of the mechanism 24, the mechanism 102 is of light weight construction, is portable so as to give an exceptional degree of mobility to its wearer, and its flow rate is individually adjustable to accommodate the desires of the wearer.

Figure 4:
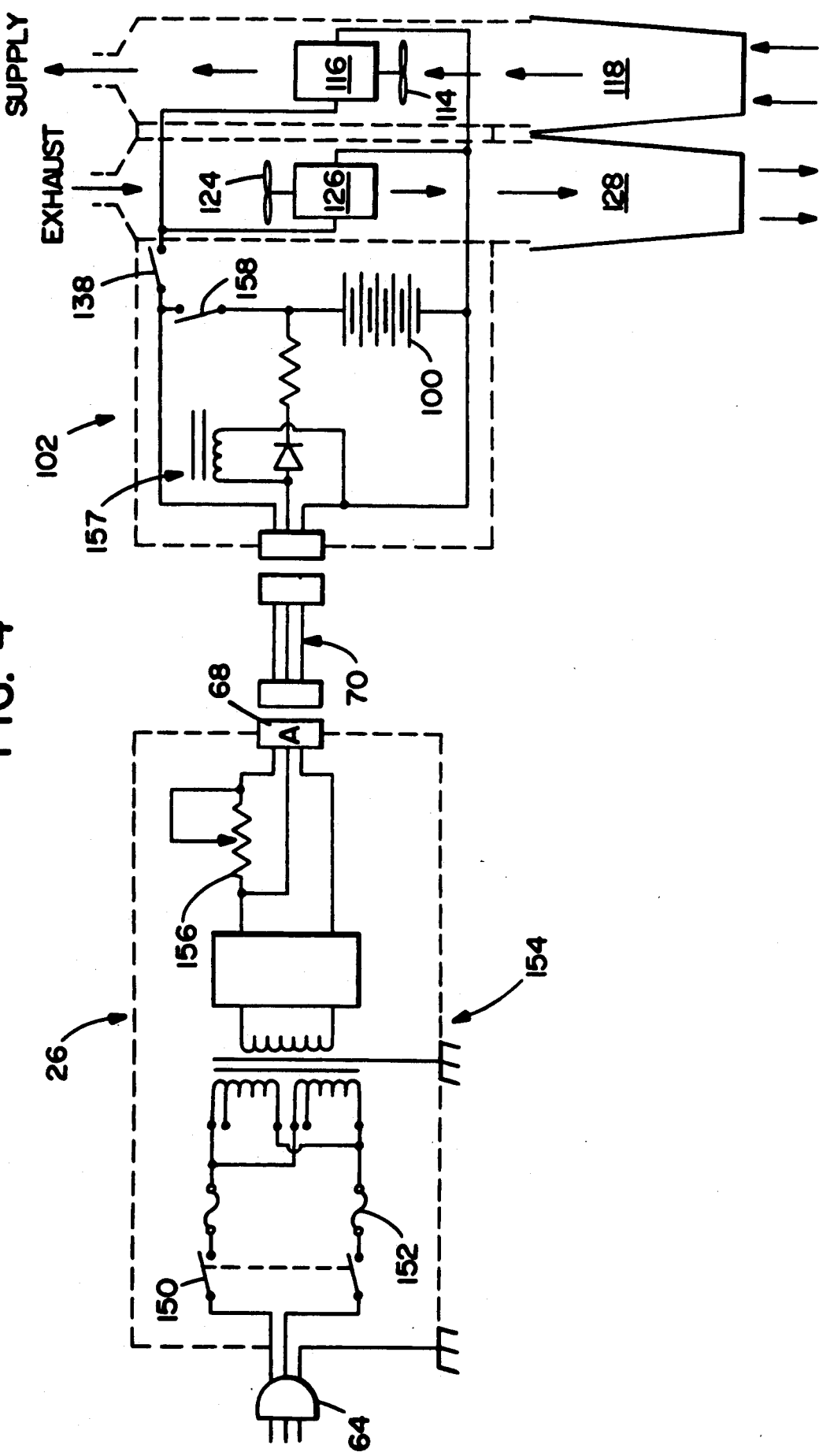
FIG. 4 is a schematic diagram of an electrical system employed in conjunction with the system of FIG. 3.

FIG. 4 is illustrative of an electrical system for powering the mechanism 102. As schematically illustrated, an on/off switch 150 may be provided on the housing for the power source 26. Only one complete circuit is illustrated, since the remaining five circuits would merely be cumulative. Protection is afforded the system by means of fuses 152 and an a.c. to d.c. converter and transformer 154 assures the conversion necessary for operation of the mechanism 102. A variable resistor 156 which is manually operable by means of the control knob 72 adjusts output voltage of the power source. Such adjustment may be, for example, between 6 and 12 volts thereby resulting in application of an appropriate electromotive force to the motors 116, 126 to assure a flow rate as desired by the wearer.

When the power cord 70 electrically connects the power source 26 and the mechanism 102, it will be appreciated that a relay 157 is energized to maintain a contact 158 in the open position. By so doing, the back-up battery 100 is disconnected from the motors 116, 126. However, when the power cord 70 is disconnected, the relay 157 is deenergized, closing the contact 158. When this occurs, the back-up battery 100 provides energy for operating the motors 116, 126. When it is desired to inactivate the mechanism 102, the switch 138 is operated. The switch 138 is situated in the electrical circuit such that, when it is open, the motors 116, 126 are deenergized from both the power source 26 and from the back-up battery 100.

It will be appreciated that a substantially similar electrical system may be used to power the mechanism 24.

While preferred embodiments of the invention have been disclosed in detail, it should be understood by those skilled in the art that various other modifications may be made to the illustrated embodiments without departing from the scope of the invention as described in the specification and defined in the appended claims.

I claim:

1. A personal ventilating system for use with a surgical hood enveloping at least the wearer's face and isolating from the surrounding atmosphere the breathing space proximate the wearer's nose and mouth, said system comprising:
    inlet means for receiving air from the breathing space isolated by the surgical hood;
    outlet means for exhausting to the surrounding atmosphere air flowing from said inlet means;
    filter means intermediate said inlet means and said outlet means for removing impurities from the air drawn from the breathing space within the surgical hood;
    adjustable flow inducing means including a fan and a variable speed d.c. motor for driving said fan operable for drawing air from the breathing space within the surgical hood and causing it to exhaust through said outlet means to the surrounding atmosphere; and
    a first power source for operating said flow inducing means to achieve a desired flow rate including a d.c. power supply distant from the wearer and having a variable speed control for selectively varying the voltage being directed to said motor;
    cord means selectively coupling said power supply and said motor;
    a second power source for operating said flow inducing means including a battery; and
    switch means for selectively energizing said motor either by said power supply or by said battery.

2. A personal ventilating system as set forth in claim 1 including:
    a support member sized and shaped to fit on the head of the wearer and including a head band adapted to generally envelop the head;
    a transparent face plate carried by said support member to extend downwardly from said support member so as to be coextensive with the face of the wearer;
    a suction ventilation conduit including said outlet means and a pressurized ventilation conduit including said inlet means, each opening into the space enclosed by said transparent face plate, each of said conduits at least in part being a flexible tube extending away from said face plate and having one end supported by said support member;
    a hood of flexible material extending over said support member to locations below said face plate adapted to enclose at least the head and shoulders of the wearer, said hood having an opening through which said face plate projects; and
    means for isolating the space enclosed by said transparent face plate from the surrounding atmosphere.

3. A personal ventilating system for use with a surgical hood enveloping at least the wearer's face and isolating from the surrounding atmosphere the breathing space proximate the wearer' nose and mouth, said system comprising:
    a first flow subsystem for delivering filtered air from the atmosphere to the breathing space isolated by the surgical hood, said first flow subsystem including:
    first inlet means for receiving air from the surrounding atmosphere;
    first outlet means for exhausting to the breathing space isolated by the surgical hood air flowing from said first inlet means;
    first filter means intermediate said first inlet means and said first outlet means for removing impurities from the air drawn from the atmosphere; and
    first adjustable flow inducing means including a first fan and a first variable speed d.c. motor for driving said first fan operable for drawing air from the surrounding atmosphere and causing it to exhaust through said first outlet means to the breathing space within the surgical hood;
    a second flow subsystem for exhausting filtered air to the atmosphere from the breathing space isolated by the surgical hood, said second flow subsystem including:
    second inlet means for receiving air from the breathing space isolated by the surgical hood;
    second outlet means for exhausting to the surrounding atmosphere air flowing from said second inlet means;
    second filter means intermediate said second inlet means and said second outlet means for removing impurities from the air drawn from the breathing space isolated by the surgical hood; and
    second adjustable flow inducing means including a second fan and a second variable speed d.c. motor for driving said second fan operable for drawing air from the surgical hood and causing it to exhaust through said second outlet means to the surrounding atmosphere; and
    a first power source for operating said first and second flow inducing means to achieve a desired flow rate including a d.c. power supply external of the wearer having a variable speed control for selectively varying the voltage being directed to said motor;
    cord means electrically coupling said power supply and said motor;
    a second power source for operating said flow inducing means including a battery; and switch means for selectively energizing said first and second motors either by said power supply or by said battery;

whereby a wearer of the surgical hood is protected against impurities in the atmosphere; and whereby a person not wearing a surgical hood but positioned proximate to the wearer of the surgical hood is protected against impurities emanating from the wearer of the surgical hood.

4. A personal ventilating system as set forth in claim 3 including:

a support member sized and shaped to fit on the head of the wearer and including a head band adapted to generally envelop the head;

a transparent face plate carried by said support member to extend downwardly from said member so as to be coextensive with the face of the wearer;

pressurized ventilation conduit means including said inlet means opening into the breathing space enclosed by said transparent face plate, said pressurized conduit means at least in part being a flexible tube extending away from said face plate and having one end supported by said support member; and suction ventilation conduit means including said outlet means opening into the space enclosed by said transparent face plate, said suction conduit means at least in part being a flexible tube extending away from said face plate and having one end supported by said support member; and a hood of flexible sheet material extending over said support member to locations below said face plate adapted to enclose a least the head and shoulders of the wearer, said hood having an opening through which said face plate projects.

* * * * *